(12) United States Patent
Nakata et al.

(10) Patent No.: US 11,253,470 B2
(45) Date of Patent: Feb. 22, 2022

(54) COMPOSITION FOR EXTERNAL APPLICATION

(71) Applicant: Kobayashi Pharmaceutical Co., Ltd., Osaka (JP)

(72) Inventors: Takahiro Nakata, Ibaraki (JP); Junji Akaki, Ibaraki (JP); Masahiro Goto, Fukuoka (JP)

(73) Assignee: Kobayashi Pharmaceutical Co., Ltd., Osaka (JP)

( * ) Notice: Subject to any disclaimer, the term of this patent is extended or adjusted under 35 U.S.C. 154(b) by 39 days.

(21) Appl. No.: 16/474,883

(22) PCT Filed: Dec. 26, 2017

(86) PCT No.: PCT/JP2017/046586
§ 371 (c)(1),
(2) Date: Jun. 28, 2019

(87) PCT Pub. No.: WO2018/124043
PCT Pub. Date: Jul. 5, 2018

(65) Prior Publication Data
US 2019/0336438 A1 Nov. 7, 2019

(30) Foreign Application Priority Data
Dec. 28, 2016 (JP) .............................. JP2016-257056

(51) Int. Cl.
| A61K 9/00 | (2006.01) |
| A61K 8/06 | (2006.01) |
| A61K 8/37 | (2006.01) |
| A61K 8/60 | (2006.01) |
| A61K 8/64 | (2006.01) |
| A61K 8/73 | (2006.01) |
| A61K 8/86 | (2006.01) |
| A61K 9/107 | (2006.01) |
| A61K 31/715 | (2006.01) |
| A61K 47/14 | (2017.01) |
| A61Q 19/00 | (2006.01) |

(52) U.S. Cl.
CPC .............. *A61K 9/0014* (2013.01); *A61K 8/06* (2013.01); *A61K 8/37* (2013.01); *A61K 8/60* (2013.01); *A61K 8/64* (2013.01); *A61K 8/73* (2013.01); *A61K 8/86* (2013.01); *A61K 9/107* (2013.01); *A61K 31/715* (2013.01); *A61K 47/14* (2013.01); *A61Q 19/00* (2013.01)

(58) Field of Classification Search
CPC ......... A61K 9/0014; A61K 9/107; A61K 8/06
See application file for complete search history.

(56) References Cited

U.S. PATENT DOCUMENTS

| 5,587,149 A | * | 12/1996 | Punto | ....................... A61K 8/06 424/59 |
| 2009/0238846 A1 | * | 9/2009 | Fujii | ....................... A61P 29/00 424/400 |
| 2014/0288191 A1 | * | 9/2014 | Kim | ........................ A61K 8/73 514/772.4 |

FOREIGN PATENT DOCUMENTS

| JP | 10-505865 A | | 6/1998 | |
| JP | 2011-037723 A | * | 2/2011 | ............. A61K 9/107 |
| JP | 2011-037723 A | | 2/2011 | |
| JP | 4843494 B2 | | 12/2011 | |
| WO | WO 96/24325 A1 | | 8/1996 | |
| WO | WO 2006/025583 A1 | | 3/2006 | |
| WO | WO 2007/070983 A1 | | 6/2007 | |

OTHER PUBLICATIONS

Shimadzu (https://www.shimadzu.com/an/service-support/technical-support/analysis-basics/basic/38/38lab.html; downloaded on Oct. 27, 2020).*
Phosphoric acid density (https://www.thomassci.com/Chemicals/Acids/_/Phosphoric-Acid-Purified?q=Phosphoric%20Acid%2085; downloaded on Oct. 27, 2020).*
https://www.redlandcitybulletin.com.au/story/6689408/the-magic-healing-powers-of-aloe-vera-its-so-natural/ (downloaded on Mar. 31, 2021).*
International Search Report for International Application No. PCT/JP2017/046586, dated Mar. 20, 2018 (in 1 page).
Office Action in Chinese Patent Application No. 201780079048.8 dated Mar. 23, 2021.

* cited by examiner

*Primary Examiner* — Pancham Bakshi
(74) *Attorney, Agent, or Firm* — Knobbe, Martens, Olson & Bear, LLP

(57) ABSTRACT

An object of the present invention is to provide a composition for external use having excellent percutaneous absorption properties. A composition for external use comprising a water-soluble fraction dispersed in an oily phase, wherein the water-soluble fraction contains a surfactant and a solution in which a water-soluble substance is dissolved in water, and the content of the water in the water-soluble fraction is 0.1 to 2.5% by weight based on the composition for external use.

6 Claims, No Drawings

COMPOSITION FOR EXTERNAL APPLICATION

TECHNICAL FIELD

The present invention relates to a composition for external use. Specifically, the present invention relates to a composition for external use having excellent percutaneous absorption properties.

BACKGROUND ART

The horny layer of the skin, which is composed of oily substances such as cholesterol and sphingolipids, is hydrophobic and dense, and prevents evaporation of moisture from inside the body. On the other hand, this structure of the horny layer becomes a barrier to the penetration of medicines for external use into the skin. In general, substances having molecular weights of more than about 500 are unlikely to penetrate into the skin. Because of this skin barrier, percutaneous absorption of water-soluble substances has been heretofore very difficult to achieve. Furthermore, dosage forms of agents for external use containing water-soluble substances are limited to lotions, gels, creams, and the like. Thus, even if such an agent for external use is applied to the skin, the water-soluble substance may be held in the water in the formulation, and prevented from migrating into the skin. As a result, the water-soluble substance is unlikely to be percutaneously absorbed.

Various studies have been made regarding methods for improving the percutaneous absorption properties of water-soluble substances. Patent Literature 1, for example, discloses a composition for skin that is suitable for percutaneous absorption, wherein a hydrophilic segment is used as a core, the hydrophilic segment being produced by mixing an oily phase containing an amphiphilic polymer in an oily base and an aqueous phase containing a water-soluble drug in an aqueous solvent, or by mixing an oily base and an aqueous phase containing an amphiphilic polymer and a water-soluble drug in an aqueous solvent; a hydrophobic segment is used as a shell; and the composition comprises a polymer reversed micelle in which the water-soluble drug is encapsulated.

Patent Literature 2, for example, discloses a S/O (Solid-in-Oil)-type external preparation having excellent percutaneous absorbability, comprising a medicine-containing complex dissolved or dispersed in an oil phase, wherein the complex contains a hydrophilic medicine covered with a surfactant, and is solid.

These compositions for external use, however, are still insufficient in terms of percutaneous absorption properties when they contain a water-soluble substance, and have room for improvement. Based on this prior art as a background, there is an earnest desire for the development of a composition for external use having excellent percutaneous absorption properties even when the composition contains a water-soluble substance.

CITATION LIST

Patent Literature

Patent Literature 1: WO 2006/25583
Patent Literature 2: Japanese Patent No. 4,843,494

SUMMARY OF INVENTION

Technical Problem

An object of the present invention is to provide a composition for external use containing a water-soluble substance and having excellent percutaneous absorption properties.

Solution to Problem

The present inventors conducted extensive research to solve the aforementioned problem, and found that a composition for external use comprising a water-soluble fraction dispersed in an oily phase, wherein the water-soluble fraction contains a surfactant and a solution in which a water-soluble substance is dissolved in water, and the content of the water in the water-soluble fraction is within a specific range, can be provided as a composition for external use having excellent percutaneous absorption properties. The present inventors also found that the composition for external use of the present invention has excellent percutaneous absorption properties even when the composition contains a water-soluble substance having a high molecular weight. The present invention has been completed as a result of further study based on these findings.

In summary, the present invention provides aspects of invention as itemized below.

Item 1. A composition for external use comprising a water-soluble fraction dispersed in an oily phase, wherein
the water-soluble fraction contains a surfactant and a solution in which a water-soluble substance is dissolved in water, and
the content of the water in the water-soluble fraction is 0.1 to 2.5% by weight based on the composition for external use.

Item 2. The composition for external use according to item 1, wherein the surfactant is a nonionic surfactant.

Item 3. The composition for external use according to item 1 or 2, wherein the surfactant is at least one selected from the group consisting of polyglycerin fatty acid esters, glycerin fatty acid esters, sorbitan fatty acid esters, polyoxyethylene hydrogenated castor oil, and sucrose fatty acid esters.

Item 4. The composition for external use according to any one of items 1 to 3, wherein the content of the surfactant is 0.1 to 20% by weight.

Item 5. The composition for external use according to any one of items 1 to 4, wherein the water-soluble substance is one selected from the group consisting of proteins and polysaccharides.

Item 6. The composition for external use according to any one of items 1 to 5, wherein the content of the water-soluble substance is 0.0001 to 2.5% by weight.

Item 7. The composition for external use according to item 6, wherein the oily phase contains a liquid oil.

Advantageous Effects of Invention

According to the present invention, there is provided a composition for external use having excellent percutaneous absorption properties. In particular, the composition for external use of the present invention has excellent percutaneous absorption properties even when it contains a water-soluble substance having a high molecular weight, and thus, can be suitably used as carriers for various drugs.

DESCRIPTION OF EMBODIMENTS

The composition for external use of the present invention is a composition for external use comprising a water-soluble fraction dispersed in an oily phase, wherein the water-soluble fraction contains a surfactant and a solution in which a water-soluble substance is dissolved in water, and the content of the water in the water-soluble fraction is 0.1 to 2.5% by weight based on the composition for external use. The composition for external use of the present invention will be hereinafter described in detail.

Water-Soluble Fraction

In the present invention, the water-soluble fraction contains a surfactant and a solution in which a water-soluble substance is dissolved in water. The water-soluble fraction contains the water-soluble substance, the water, and the surfactant as main components. It is assumed that the water-soluble fraction is in the state of a particle wherein the hydrophilic moiety of the surfactant is associated with the solution in which the water-soluble substance is dissolved in water, and coats the surroundings of the solution, or, even if the coating is not formed, the water-soluble fraction is dispersed in the oily phase. Each of the components of the composition for external use of the present invention will be described.

(Water-Soluble Substance)

The water-soluble substance to be used in the present invention is not particularly limited as long as it exhibits water solubility, and is pharmacologically or cosmetically acceptable; examples include a water-soluble substance that dissolves in water (20° C.) at a ratio of 1 g or more of the water-soluble substance to 100 g of the water, preferably 1 g or more of the water-soluble substance to 30 g of the water, and more preferably 1 g or more of the water-soluble substance to 10 g of the water.

In the present invention, as the water-soluble substance, a water-soluble substance is suitably used that exhibits pharmacological or cosmetic efficacy, and is used as an active ingredient for compositions for external use. This water-soluble substance is not particularly limited in type, and may be any of a low-molecular-weight substance having a molecular weight of less than about 500 Da and a high-molecular-weight substance having a molecular weight of about 500 Da or more.

Specific examples of the low-molecular-weight substance to be used as the water-soluble substance include whitening agents, such as L-ascorbic acid, sodium L-ascorbate, L-ascorbic acid monophosphate, L-ascorbic acid-2-sulfate, L-ascorbic acid glucoside, arbutin, kojic acid, kojic acid monobutyrate, kojic acid monocaprate, kojic acid monopalmitate, kojic acid monostearate, kojic acid monocinnamoate, kojic acid monobenzoate, kojic acid dibutyrate, kojic acid dipalmitate, kojic acid distearate, kojic acid dioleate, and tranexamic acid; antiinflammatory agents, such as dipotassium glycyrrhizinate, ammonium glycyrrhizinate, glycyrrhetic acid, allantoin, salicylic acid, glycol salicylate, methyl salicylate, indomethacin, felbinac, diclofenac sodium, and loxoprofen sodium; antihistamines, such as diphenhydramine hydrochloride and chlorpheniramine maleate; local anesthetics, such as lidocaine, dibucaine, procaine, tetracaine, bupivacaine, mepivacaine, and chloroprocaine; bactericidal/antimicrobial agents, such as benzalkonium chloride, dequalinium chloride, benzethonium chloride, cetylpyridinium chloride, isopropylmethylphenol, chlorhexidine hydrochloride, chlorhexidine gluconate, croconazole hydrochloride, and zinc pyrithione; blood circulation promoters, such as nonanoic acid vanillylamide, benzyl nicotinate, cepharanthine, and carpronium chloride; antibiotics, such as tetracycline hydrochloride; hormonal agents, such as oxytocin, corticotropin, vasopressin, secretin, gastrin, and calcitonin; B vitamins and derivatives thereof, such as vitamin B1, vitamin B2, niacin, pantothenic acid, panthenol, vitamin B6, biotin, folic acid, nicotinic acid, nicotinamide, and vitamin $B_{12}$; monosaccharides, such as glucosamine, N-acetyl glucosamine, glucose, and fructose; disaccharides, such as maltose, sucrose, lactose, and trehalose; oligosaccharides, such as malto-oligosaccharides, galacto-oligosaccharides, agaro-oligosaccharide, and xylo-oligosaccharides; and amino acids. These low-molecular-weight compounds may be used alone or in combinations of two or more.

Specific examples of the high-molecular-weight substance to be used as the water-soluble substance include proteins, such as collagen, cytokines, antibodies, vaccine antigens, albumin, and enzymes (such as trypsin, lysozyme chloride, chymotrypsin, semi-alkaline proteinase, serrapeptase, lipase, and hyaluronidase); polysaccharides, such as heparinoids, hyaluronic acid, chondroitin sulfate, chitosan, chitin, glycogen, carrageenan, fucoidan, porphyran, xanthan gum, tuberose polysaccharides, quince seed extract, gellan gum, alginic acid, pectin, carboxymethyl cellulose, hydroxyethyl cellulose, hydroxypropyl cellulose, guar gum, agarose, chitosan, pullulan, locust bean gum, galactan, gum arabic, tara gum, tamarind seed gum, and salts thereof (such as alkali metal salts, for example, sodium salt and potassium salt); and aloe extract. These high-molecular-weight compounds may be used alone or in combinations of two or more.

These water-soluble substances may be used alone or in combinations of two or more.

With conventional percutaneous absorption technologies, percutaneous absorption of water-soluble high-molecular-weight substances, such as proteins and polysaccharides, has been very difficult to achieve; however, with the composition for external use of the present invention, even such water-soluble high-molecular-weight substances can be effectively percutaneously absorbed. In view of this effect of the present invention, the water-soluble substance is preferably a water-soluble high-molecular-weight substance, and more preferably a protein or a polysaccharide, for example.

In the composition for external use of the present invention, the water-soluble fraction contains the solution in which the water-soluble substance is dissolved in water. The content of the water-soluble substance in the solution contained in the water-soluble fraction is, for example, 0.001 to 60% by weight, preferably 0.001 to 50% by weight, more preferably 0.001 to 40% by weight, still more preferably 1 to 40% by weight, and particularly preferably 10 to 40% by weight.

The content of the water-soluble substance in the composition for external use of the present invention may be appropriately set, in accordance with the use of the composition for external use, the type of the surfactant to be used, and the like; for example, the content is 0.0001 to 2.5% by weight, preferably 0.0001 to 2% by weight, and more preferably 0.0001 to 1.5% by weight.

(Surfactant)

The surfactant to be used in the present invention is not particularly limited as long as it can achieve a water-in-oil-type emulsion, and examples include known surfactants, such as nonionic surfactants, anionic surfactants, cationic surfactants, and amphoteric surfactants. Among the above, a nonionic surfactant is preferred, in order to further improve the percutaneous absorption properties of the composition for external use.

Examples of the nonionic surfactant that is typically used to form the composition for external use of the present invention into a water-in-oil type include polyglycerin fatty acid esters, glycerin fatty acid esters, sorbitan fatty acid esters, propylene glycol fatty acid esters, polyoxyethylene hydrogenated castor oil, polyoxyethylene polyoxypropylene alkyl ethers, and sucrose fatty acid esters.

A polyglycerin fatty acid ester is an ester of a fatty acid and polyglycerin. In the polyglycerin fatty acid ester, the number of ester bonds (the number of fatty acids attached to one molecule of polyglycerin) is, for example, 1 to 10, preferably 1 to 6, and more preferably 1 to 3. The number of carbon atoms in the fatty acid constituting the polyglycerin fatty acid ester is, for example, 6 to 24, preferably 8 to 22, and more preferably 12 to 18. Furthermore, the degree of polymerization of polyglycerin constituting the polyglycerin fatty acid ester is, for example, 2 to 30, and preferably 2 to 10. Specific examples of the polyglycerin fatty acid ester include polyglyceryl-2 stearate (diglyceryl monostearate), polyglyceryl-2 oleate (diglyceryl monooleate), polyglyceryl-4 oleate (tetraglyceryl monooleate), polyglyceryl-10 oleate (decaglyceryl monooleate), polyglyceryl-10 trioleate (decaglyceryl trioleate), polyglyceryl-10 palmitate (decaglyceryl monopalmitate), polyglyceryl-2 isostearate, polyglyceryl-2 triisostearate, polyglyceryl-4 stearate, polyglyceryl-6 tristearate, polyglyceryl-10 pentastearate, polyglyceryl-10 pentahydroxystearate, polyglyceryl-10 pentastearate, polyglyceryl-10 pentaoleate, polyglyceryl-6 polyricinoleate, and polyglyceryl-10 polyricinoleate. Among these polyglycerin fatty acid esters, for example, polyglyceryl-2 stearate, polyglyceryl-2 oleate, polyglyceryl-4 oleate, polyglyceryl-10 oleate, polyglyceryl-10 trioleate, and polyglyceryl-10 palmitate are preferred.

A glycerin fatty acid ester is a mono-, di-, or tri-ester of a fatty acid and glycerin. The number of carbon atoms in the fatty acid constituting the glycerin fatty acid ester is, for example, 6 to 24, preferably 8 to 22, and more preferably 12 to 18. Specific examples of the glycerin fatty acid ester include glyceryl monomyristate, glyceryl monostearate, glyceryl monoisostearate, glyceryl monooleate, glyceryl dioleate, glyceryl trioleate, and glyceryl distearate. Among these glycerin fatty acid esters, for example, glyceryl monooleate, glyceryl distearate, and glyceryl monomyristate are preferred.

A sorbitan fatty acid ester is a mono-, di-, or tri-ester of a fatty acid and sorbitan. The number of carbon atoms in the fatty acid constituting the sorbitan fatty acid ester is, for example, 6 to 24, preferably 8 to 22, and more preferably 12 to 18. Specific examples of the sorbitan fatty acid ester include sorbitan monostearate, sorbitan monoisostearate, sorbitan sesquiisostearate, sorbitan sesquioleate, sorbitan monooleate, sorbitan trioleate, sorbitan monopalmitate, and sorbitan monolaurate. Among these sorbitan fatty acid esters, for example, sorbitan monooleate, sorbitan trioleate, sorbitan monostearate, sorbitan monopalmitate, and sorbitan monolaurate are preferred.

A propylene glycol fatty acid ester is a mono- or di-ester of a fatty acid and propylene glycol. The number of carbon atoms in the fatty acid constituting the propylene glycol fatty acid ester is, for example, 6 to 24, preferably 8 to 22, and more preferably 12 to 18. Specific examples of the propylene glycol fatty acid ester include propylene glycol monostearate, propylene glycol monoisostearate, and propylene glycol monooleate.

Polyoxyethylene hydrogenated castor oil is a compound in which hydrogenated castor oil has been etherified with a polyoxyethylene chain. The addition molar number of ethylene oxide of the polyoxyethylene chain in polyoxyethylene hydrogenated castor oil is, for example, 5 to 100, preferably 10 to 80, and more preferably 20 to 60. Specific examples of polyoxyethylene hydrogenated castor oil include PEG-5 hydrogenated castor oil, PEG-10 hydrogenated castor oil, and PEG-60 hydrogenated castor oil (polyoxyethylene hydrogenated castor oil 60). Among these types of polyoxyethylene hydrogenated castor oil, PEG-60 hydrogenated castor oil, for example, is preferred.

A polyoxyethylene polyoxypropylene alkyl ether is a compound in which a polyoxyethylene polyoxypropylene chain is attached to an alkyl group through an ether bond. Specific examples of the polyoxyethylene polyoxypropylene alkyl ether include PPG-4 ceteth-1.

A sucrose fatty acid ester is an ester of a fatty acid and sucrose. The number of carbon atoms in the fatty acid constituting the sucrose fatty acid ester is, for example, 6 to 24, preferably 8 to 22, and more preferably 12 to 18. Specific examples of the sucrose fatty acid ester include sucrose stearate, sucrose erucate, sucrose laurate, sucrose behenate, sucrose palmitate, and sucrose oleate. Among these sucrose fatty acid esters, sucrose erucate, for example, is preferred.

From the viewpoint of further improving the percutaneous absorption properties of the water-soluble substance, among these nonionic surfactants, preferred are polyglycerin fatty acid esters, glycerin fatty acid esters, sorbitan fatty acid esters, polyoxyethylene hydrogenated castor oil, and sucrose fatty acid esters; more preferred are polyglycerin fatty acid esters and glycerin fatty acid esters; and particularly preferred are polyglycerin fatty acid esters.

Among these nonionic surfactants, suitable specific examples include polyglyceryl-2 stearate, polyglyceryl-2 oleate, polyglyceryl-4 oleate, polyglyceryl-10 oleate, polyglyceryl-10 trioleate, polyglyceryl-10 palmitate, glyceryl monostearate, glyceryl monooleate, glyceryl distearate, glyceryl monomyristate, sorbitan monooleate, sorbitan trioleate, sorbitan monostearate, sorbitan monopalmitate, sorbitan monolaurate, PEG-60 hydrogenated castor oil, and sucrose erucate; more preferred are polyglyceryl-4 oleate, polyglyceryl-10 oleate, polyglyceryl-10 trioleate, polyglyceryl-10 palmitate, glyceryl monooleate, sorbitan monooleate, sorbitan trioleate, and sorbitan monolaurate; and particularly preferred are polyglyceryl-4 oleate, polyglyceryl-10 oleate, polyglyceryl-10 trioleate, polyglyceryl-10 palmitate, and glyceryl monooleate.

These nonionic surfactants may be used alone or in combinations of two or more.

The content of the nonionic surfactant in the composition for external use of the present invention may be appropriately set, in accordance with the type of the surfactant to be used; for example, the content is 0.1 to 20% by weight, preferably 0.5 to 10% by weight, and more preferably 1.5 to 7.5% by weight.

(Aqueous-Phase Base)

The composition for external use of the present invention contains water as an aqueous-phase base of the water-soluble fraction. In the composition for external use of the present invention, the content of the water in the water-soluble fraction is 0.1 to 2.5% by weight based on the composition for external use. Because the composition for external use of the present invention contains water in a predetermined range of amounts, it has excellent percutaneous absorption properties. The content of the water in the water-soluble fraction is preferably 0.5 to 2% by weight, more preferably 0.75 to 1.25% by weight, and still more preferably 0.75 to 1% by weight, for example, based on the composition for external use, in order to further improve the percutaneous absorption properties.

Oily Phase

Examples of an oily-phase base in the composition for external use of the present invention include oily components, such as liquid oils, solid oils, and higher alcohols.

A liquid oil is an oil that maintains a liquid form at 25° C. The liquid oil to be used in the present invention may be a liquid oil that is generally used in cosmetic preparations, pharmaceuticals for external use, and the like; examples include vegetable oils, such as avocado oil, camellia oil, macadamia nut oil, olive oil, almond oil, soybean oil, jojoba oil, cotton seed oil, rapeseed oil, sesame oil, perilla oil, cinnamon oil, corn oil, peanut oil, sunflower oil, cacao oil, mentha oil, bergamot oil, and fennel oil; fatty acids, such as oleic acid and isostearic acid; ester oils, such as cetyl ethylhexanoate, ethylhexyl palmitate, octyldodecyl myristate, neopentyl glycol diethylhexanoate, glyceryl tri-2-ethylhexanoate, octyldodecyl oleate, isopropyl myristate, glyceryl triisostearate, and glyceryl monoethylhexanoate-di-para-methoxycinnamate; silicone oils, such as dimethylpolysiloxane, methyl hydrogen polysiloxane, methylphenylpolysiloxane, and octamethylcyclotetrasiloxane; and liquid hydrocarbon oils, such as liquid paraffin, squalene, and squalane. These liquid oils may be used alone or in combinations of two or more.

Among these liquid oils, preferred are vegetable oils, ester oils, and liquid hydrocarbon oils; more preferred are almond oil, olive oil, soybean oil, octyldodecyl myristate, glyceryl tri-2-ethylhexanoate, octyldodecyl oleate, isopropyl myristate, glyceryl triisostearate, and liquid paraffin; and particularly preferred are isopropyl myristate, olive oil, almond oil, and soybean oil.

A solid oil is an oil that maintains a solid form at 25° C. The solid oil to be used in the present invention may be a solid oil that is generally used in cosmetic preparations, pharmaceuticals for external use, and the like; examples include solid oils such as candelilla wax, rice bran wax, beeswax, cotton wax, carnauba wax, lanolin, shellac wax, ozokerite, ceresin, polyethylene wax, microcrystalline wax, paraffin, vaseline, lauric acid, myristic acid, palmitic acid, stearic acid, behenic acid, 12-hydroxystearic acid, undecylenic acid, myristyl myristate, cetyl myristate, stearyl stearate, cetyl stearate, cetyl palmitate, cholesteryl stearate, cholesteryl oleate, dextrin palmitate, stearoyl inulin, hydrogenated jojoba oil, ceresin wax, solid paraffin wax, polyethylene wax, and silicone wax. These solid oils may be used alone or in combinations of two or more.

Among these solid oils, preferred are vaseline, paraffin, cholesteryl stearate, dextrin palmitate, and microcrystalline wax; and more preferred are vaseline, dextrin palmitate, and microcrystalline wax.

A higher alcohol is a monohydric alcohol having six or more carbon atoms in one molecule. While the number of carbon atoms in one molecule of the higher alcohol to be used in the present invention may be six or more, it is preferably 6 to 34, and more preferably 14 to 22, for example.

The higher alcohol to be used in the present invention may be a higher alcohol that is generally used in cosmetic preparations, pharmaceuticals for external use, and the like; examples include straight-chain higher alcohols, such as lauryl alcohol, cetyl alcohol, stearyl alcohol, behenyl alcohol, myristyl alcohol, cetostearyl alcohol, cetanol, and oleyl alcohol; and branched-chain higher alcohols, such as glycerin monostearyl ether (batyl alcohol). These higher alcohols may be used alone or in combinations of two or more.

Among these oily-phase bases, for example, a liquid oil is preferred.

The content of the oily-phase base in the composition for external use of the present invention is not particularly limited, and may be appropriately set, in accordance with the type of the oily-phase base to be used, the form of the composition for external use, the use of the composition for external use, and the like; for example, the content is 50 to 99.9% by weight, preferably 60 to 99.9% by weight, and more preferably 70 to 99.9% by weight.

Other Components

The composition for external use of the present invention may optionally contain, in addition to the above-described components, other bases and additives that are required for, for example, formulation into a pharmaceutical preparation. These additives are not particularly limited as long as they are pharmacologically or cosmetically acceptable; examples include preservatives (such as methylparaben, propylparaben, benzoic acid, sodium benzoate, and sorbic acid), fragrances (such as citral, 1,8-cineol, citronellal, and farnesol), colorants (such as tar dyes (for example, Brown No. 201, Blue No. 201, Yellow No. 4, and Yellow No. 403), cacao color, chlorophyll, and aluminum oxide), thickening agents (such as carboxyvinyl polymer, hydroxypropylmethylcellulose, polyvinyl pyrrolidone, sodium alginate, ethyl cellulose, carboxymethylcellulose sodium, xanthan gum, and carrageenan), pH adjusters (such as phosphoric acid, hydrochloric acid, citric acid, sodium citrate, succinic acid, tartaric acid, sodium hydroxide, potassium hydroxide, triethanolamine, and triisopropanolamine), humectants (such as sodium dl-pyrrolidone carboxylate solution, D-sorbitol solution, and macrogol), stabilizers (such as dibutylhydroxytoluene, butylated hydroxyanisole, disodium edetate, sodium metaphosphate, L-arginine, L-aspartic acid, DL-alanine, glycine, sodium erythorbate, propyl gallate, sodium sulfite, sulfur dioxide, chlorogenic acid, catechin, and rosemary extract), polyhydric alcohols (such as glycerin, propylene glycol, dipropylene glycol, butylene glycol, and polyethylene glycol), antioxidants, ultraviolet absorbers, chelating agents, binders, buffers, solubilizing agents, and antiseptics.

Emulsification Type, Product Forms, and Use

The composition for external use of the present invention is in the form of a dispersion of the water-soluble fraction in the oily phase, and thus, is a water-in-oil-type (W/O-type) emulsion. Because the composition for external use of the present invention is of the water-in-oil type, the percutaneous absorption properties of the composition for external use containing the water-soluble substance can be effectively improved. The composition for external use of the present invention may also be formulated into a W/O/W-type pharmaceutical preparation, by further dispersing the composition in the aqueous phase in accordance with a conventional method.

The composition for external use of the present invention can be used as an agent for external use such as, for example, a cosmetic preparation or a pharmaceutical for external use. While the product form of the composition for external use of the present invention is not particularly limited, examples include creams, ointments, emulsions, gels, oils, lotions, liniments, and aerosols. Among the above, for example, creams, ointments, emulsions, oils, and lotions are preferred.

The use of the composition for external use of the present invention can be appropriately designed, in accordance with the component as the water-soluble substance to be encapsulated. Furthermore, the composition for external use of the present invention can be used as a drug carrier, because it has excellent percutaneous absorption properties, and a water-soluble substance having a relatively high molecular weight can be encapsulated therein.

Production Method

The composition for external use of the present invention can be produced in accordance with a known technique for formulating compositions for external use. Examples of the method for producing the composition for external use of the present invention include a method in which the components to be incorporated are divided into water-soluble components and oily components, an aqueous phase containing the water-soluble components and an oily phase containing the oily components are prepared, and these phases are emulsified in accordance with a known technique. Specifically, the composition for external use of the present invention can be produced by preparing the aqueous phase in which the water-soluble substance is dissolved in water, preparing the oily phase containing the surfactant and the oily-phase base, and mixing and emulsifying the prepared aqueous phase and oily phase.

EXAMPLES

The present invention will be described next in more detail with reference to examples, although the invention is in no way limited thereto.

Experimental Example 1

<Preparation of Compositions for External Use>

A heparinoid was weighed into a tube to give the formulation shown in each of Tables 2 to 6, purified water was added thereto, and the heparinoid was dissolved using a vortexer to prepare an aqueous solution of the heparinoid. Next, an oily-phase base was weighed into a beaker to give the amount shown in each of Tables 2 to 6, and heated in a hot water bath (80° C.) for 5 minutes or longer, under stirring with a stirrer. Into the beaker, a surfactant dissolved in advance by heating in a hot water bath (70° C.) was added in the amount shown in each of Tables 2 to 6, and heated in a hot water bath (80° C.) for 10 minutes or longer, under stirring with a stirrer. Then, the beaker was removed from the hot water bath, and 1 ml of the aqueous solution of the heparinoid prepared above was slowly added dropwise, under stirring, into the beaker. This mixture was stirred until it was cooled to room temperature, thereby obtaining a composition for external use containing a water-soluble substance in the form of a water-in-oil-type emulsion.

<Evaluation of Percutaneous Absorption Properties>

(Percutaneous Absorption Test)

A percutaneous absorption test was performed using a Franz cell, in accordance with the following procedure: A vertical Franz cell (model: TP-8S, manufactured by VIDREX) was fixed on a stirrer, and connected to a water bath and kept at about 32° C. Skin (diameter: about 1.5 cm) excised from a hairless mouse (Hos: HR-1) was placed in the Franz cell with the horny layer facing upward. The cap of the Franz cell was placed thereon and fixed with a clamp. Next, the receptor was filled with phosphate buffer (PBS), while avoiding the entry of air. Then, 1 ml (1 g) of each of the compositions for external use obtained above was applied to the donor (1.77 cm$^2$). After a lapse of a sampling time, 300 µl of the receptor solution was collected, and fresh PBS was supplied instead. The above procedure was repeated, and the test was performed until an end time (24 hours).

(Measurement of the Amount of Percutaneous Absorption (Amount of Permeation of Heparinoid)

The amount of the heparinoid percutaneously absorbed was determined by the colorimetric method described below, using the measurement kit "Test Team Heparin S" (manufactured by Sekisui Medical Co., Ltd.).

(1) Preparation of Reagents

Using the above-mentioned measurement kit, reagents were prepared as shown in Table 1 below.

TABLE 1

| | |
|---|---|
| Antithrombin III solution | 10 ml of distilled water was added to the vial, and the contents were dissolved. |
| Factor Xa solution | 10 ml of distilled water was added to the vial, and the contents were dissolved. |
| Substrate solution | 20 ml of distilled water was added to the vial, and the contents were dissolved. |
| Quenching solution | 20 ml of distilled water was added to 20 ml of acetic acid and mixed. |

(2) Preparation of Standard Solutions

Using Test Team Heparin S (manufactured by Sekisui Medical Co., Ltd.), and PBS as a solvent, standard solutions for the calibration curves at eight points, i.e., 0, 0.03, 0.1, 0.3, 1, 3, 10, and 30 µg/mL, were prepared.

(3) Measurement Method

To each well of a 96-well plate warmed to 37° C., 5 µl of the antithrombin III solution was added, and then 45 µl of each of the standard solutions or the sample (receptor solution) was added. The plate was sealed, and mixed on a plate shaker for 10 seconds and then warmed at 37° C. for about 2 to 6 minutes. Then, 25 µl of the Factor Xa solution was added to each well, and the plate was mixed again on the plate shaker for 10 seconds and warmed at 37° C. for about 30 seconds. Then, 50 µl of the substrate solution was added to each well, and the plate was mixed again on the plate shaker for 10 seconds and warmed at 37° C. for 3 minutes. After 3 minutes of warming, 75 µl of the quenching solution was added to each well, and the plate was mixed on the plate shaker for 10 seconds. Thereafter, absorbance at 405 nm was read by a plate reader (GENios manufactured by TECAN), and the heparinoid concentration was determined based on the calibration curves. The percutaneous absorption properties were evaluated as follows: "x": The amount of permeation of the heparinoid after 24 hours was 0 µg. "Δ": The amount of permeation of the heparinoid after 24 hours was more than 0 to 1.26 µg. "O": The amount of permeation of the heparinoid after 24 hours was more than 1.26 to 2.52 µg. "⊙": The amount of permeation of the heparinoid after 24 hours was more than 2.52 µg.

TABLE 2

| | | Examples | | | | | | | | | | | | |
|---|---|---|---|---|---|---|---|---|---|---|---|---|---|---|
| | | 1 | 2 | 3 | 4 | 5 | 6 | 7 | 8 | 9 | 10 | 11 | 12 | 13 |
| Oily-Phase Base | Isopropyl Myristate | 96.2 | 95.95 | 95.2 | 94.7 | 92.7 | 96.7 | 95.7 | 94.7 | 94.2 | 91.2 | — | — | — |
| | Squalane | — | — | — | — | — | — | — | — | — | — | 94.2 | — | — |
| | Light Liquid Paraffin | — | — | — | — | — | — | — | — | — | — | — | 94.2 | — |

TABLE 2-continued

|  |  | Examples |  |  |  |  |  |  |  |  |  |  |  |  |
|---|---|---|---|---|---|---|---|---|---|---|---|---|---|---|
|  |  | 1 | 2 | 3 | 4 | 5 | 6 | 7 | 8 | 9 | 10 | 11 | 12 | 13 |
|  | Liquid Paraffin | — | — | — | — | — | — | — | — | — | — | — | — | — |
|  | Almond Oil | — | — | — | — | — | — | — | — | — | — | — | — | 94.2 |
|  | Olive Oil | — | — | — | — | — | — | — | — | — | — | — | — | — |
|  | Soybean Oil | — | — | — | — | — | — | — | — | — | — | — | — | — |
| Surfactant | Glyceryl Monooleate | 3 | 3 | 3 | 3 | 6 | 2 | 3 | 4 | 4.5 | 7.5 | 4.5 | 4.5 | 4.5 |
| Aqueous-Phase Base | Water | 0.5 | 0.75 | 1.5 | 2 | 1 | 1 | 1 | 1 | 1 | 1 | 1 | 1 | 1 |
| Water-Soluble Substance | Heparinoid | 0.3 | 0.3 | 0.3 | 0.3 | 0.3 | 0.3 | 0.3 | 0.3 | 0.3 | 0.3 | 0.3 | 0.3 | 0.3 |
|  | Total (Weight %) | 100 | 100 | 100 | 100 | 100 | 100 | 100 | 100 | 100 | 100 | 100 | 100 | 100 |
| Percutaneous Absorption Properties | Amount of Permeation (µg) after 24 Hours | 4.06 | 7.97 | 3.01 | 4.01 | 12.9 | 8.9 | 11.5 | 11.9 | 32.84 | 5.32 | 1.3 | 2.12 | 20.67 |
|  | Evaluation of Percutaneous Absorption Properties | ◎ | ◎ | ◎ | ◎ | ◎ | ◎ | ◎ | ◎ | ◎ | ◎ | ○ | ○ | ◎ |

TABLE 3

|  |  | Examples |  |  |  |  |  |  |  |
|---|---|---|---|---|---|---|---|---|---|
|  |  | 14 | 15 | 16 | 17 | 18 | 19 | 20 | 21 |
| Oily-Phase Base | Isopropyl Myristate | — | — | 40 | 43 | 43 | 43 | 43 | 43 |
|  | Squalane | — | — | — | — | — | — | — | — |
|  | Light Liquid Paraffin | — | — | — | — | 5 | 10 | 2 | — |
|  | Liquid Paraffin | — | — | 54.2 | — | — | — | — | — |
|  | Almond Oil | — | — | — | 51.2 | 46.2 | 41.2 | 49.2 | 52.7 |
|  | Olive Oil | 94.2 | — | — | — | — | — | — | — |
|  | Soybean Oil | — | 94.2 | — | — | — | — | — | — |
| Surfactant | Glyceryl Monooleate | 4.5 | 4.5 | 4.5 | 4.5 | 4.5 | 4.5 | 4.5 | 3 |
| Aqueous-Phase Base | Water | 1 | 1 | 1 | 1 | 1 | 1 | 1 | 1 |
| Water-Soluble Substance | Heparinoid | 0.3 | 0.3 | 0.3 | 0.3 | 0.3 | 0.3 | 0.3 | 0.3 |
|  | Total (Weight %) | 100 | 100 | 100 | 100 | 100 | 100 | 100 | 100 |
| Percutaneous Absorption Properties | Amount of Permeation (µg) after 24 Hours | 9.6 | 18.81 | 4.97 | 2.12 | 1.96 | 3.97 | 3.01 | 4.21 |
|  | Evaluation of Percutaneous Absorption Properties | ◎ | ◎ | ◎ | ○ | ○ | ◎ | ◎ | ◎ |

TABLE 4

|  |  | Examples |  |  |  |  |  |  |  |  |  |
|---|---|---|---|---|---|---|---|---|---|---|---|
|  |  | 22 | 23 | 24 | 25 | 26 | 27 | 28 | 29 | 30 | 31 |
| Oily-Phase Base | Isopropyl Myristate | 94.2 | 94.2 | 95.7 | 94.2 | 95.7 | 94.2 | 94.2 | 95.7 | 94.2 | 94.2 |
| Surfactant | Sucrose Erucate | 4.5 | — | — | — | — | — | — | — | — | — |
|  | Polyoxyethylene Hydrogenated Castor Oil 60 | — | 4.5 | — | — | — | — | — | — | — | — |
|  | Diglyceryl Monooleate | — | — | 3 | 4.5 | — | — | — | — | — | — |
|  | Tetraglyceryl Monooleate | — | — | — | — | 3 | 4.5 | — | — | — | — |
|  | Decaglyceryl Monooleate | — | — | — | — | — | — | 4.5 | — | — | — |
|  | Decaglyceryl Trioleate | — | — | — | — | — | — | — | 3 | 4.5 | — |
|  | Sorbitan Monooleate | — | — | — | — | — | — | — | — | — | 4.5 |
| Aqueous-Phase Base | Water | 1 | 1 | 1 | 1 | 1 | 1 | 1 | 1 | 1 | 1 |

TABLE 4-continued

|  |  | Examples | | | | | | | | | |
|---|---|---|---|---|---|---|---|---|---|---|---|
|  |  | 22 | 23 | 24 | 25 | 26 | 27 | 28 | 29 | 30 | 31 |
| Water-Soluble Substance | Heparinoid | 0.3 | 0.3 | 0.3 | 0.3 | 0.3 | 0.3 | 0.3 | 0.3 | 0.3 | 0.3 |
|  | Total (Weight %) | 100 | 100 | 100 | 100 | 100 | 100 | 100 | 100 | 100 | 100 |
| Percutaneous Absorption Properties | Amount of Permeation (μg) after 24 Hours | 3.29 | 2.34 | 2.86 | 3.55 | 21.43 | 5.05 | 35.31 | 22.03 | 3.49 | 5.51 |
|  | Evaluation of Percutaneous Absorption Properties | ◎ | ○ | ◎ | ◎ | ◎ | ◎ | ◎ | ◎ | ◎ | ◎ |

TABLE 5

|  |  | Examples | | | | | | | | | |
|---|---|---|---|---|---|---|---|---|---|---|---|
|  |  | 32 | 33 | 34 | 35 | 36 | 37 | 38 | 39 | 40 | 41 |
| Oily-Phase Base | Isopropyl Myristate | 94.2 | 94.2 | 94.2 | 94.2 | 94.2 | 94.2 | 94.2 | 94.2 | 94.2 | 92.7 |
| Surfactant | Sorbitan Trioleate | 4.5 | — | — | — | — | — | — | — | — | — |
|  | Glyceryl Monostearate | — | 4.5 | — | — | — | — | — | — | — | — |
|  | Diglyceryl Monostearate | — | — | 4.5 | — | — | — | — | — | — | — |
|  | Glyceryl Distearate | — | — | — | 4.5 | — | — | — | — | — | — |
|  | Sorbitan Monostearate | — | — | — | — | 4.5 | — | — | — | — | — |
|  | Glyceryl Monomyristate | — | — | — | — | — | 4.5 | — | — | — | — |
|  | Decaglyceryl Monopalmitate | — | — | — | — | — | — | 4.5 | — | — | — |
|  | Sorbitan Monopalmitate | — | — | — | — | — | — | — | 4.5 | — | — |
|  | Sorbitan Monolaurate | — | — | — | — | — | — | — | — | 4.5 | — |
|  | Glyceryl Monooleate | — | — | — | — | — | — | — | — | — | 4.5 |
| Aqueous-Phase Base | Water | 1 | 1 | 1 | 1 | 1 | 1 | 1 | 1 | 1 | 2.5 |
| Water-Soluble Substance | Heparinoid | 0.3 | 0.3 | 0.3 | 0.3 | 0.3 | 0.3 | 0.3 | 0.3 | 0.3 | 0.3 |
|  | Total (Weight %) | 100 | 100 | 100 | 100 | 100 | 100 | 100 | 100 | 100 | 100 |
| Percutaneous Absorption Properties | Amount of Permeation (μg) after 24 Hours | 8.66 | 3.57 | 4.05 | 3.81 | 3.51 | 3.00 | 24.25 | 2.95 | 5.63 | 4.78 |
|  | Evaluation of Percutaneous Absorption Properties | ◎ | ◎ | ◎ | ◎ | ◎ | ◎ | ◎ | ◎ | ◎ | ◎ |

TABLE 6

|  |  | Comparative Examples | | | |
|---|---|---|---|---|---|
|  |  | 1 | 2 | 3 | 4 |
| Oily-Phase Base | Isopropyl Myristate | 93.7 | 72.5 | 99.7 | — |
|  | Squalane | — | — | — | — |
|  | Light Liquid Paraffin | — | — | — | — |
|  | Liquid Paraffin | — | — | — | — |
|  | Almond Oil | — | — | — | 99.7 |
|  | Olive Oil | — | — | — | — |
|  | Soybean Oil | — | — | — | — |
| Surfactant | Glyceryl Monooleate | — | — | — | — |
|  | Polyoxyethylene Hydrogenated Castor Oil 10 | 3 | 20 | — | — |
| Aqueous-Phase Base | Water | 3 | 7 | — | — |
| Water-Soluble Substance | Heparinoid | 0.3 | 0.5 | 0.3 | 0.3 |
|  | Total (Weight %) | 100 | 100 | 100 | 100 |
| Percutaneous Absorption Properties | Amount of Permeation (μg) after 24 Hours | 0 | 0 | 1.26 | 0.70 |
|  | Evaluation of Percutaneous Absorption Properties | X | X | Δ | Δ |
| Notes | Properties of Water-Soluble Substance | Dissolved | Dissolved | Undissolved | Undissolved |

The results are shown in Tables 2 to 6. As is evident from Tables 2 to 6, the compositions for external use of the present invention, wherein the water-soluble fraction containing the solution in which the water-soluble substance is dissolved in water is dispersed in the oily phase, were confirmed to have excellent percutaneous absorption properties.

Experimental Example 2

<Preparation of Compositions for External Use>
Water-in-oil-type compositions for external use were obtained as in Experimental Example 1, except that the components were weighed to give the formulations shown in Table 7, and fluorescein (uranine) was used instead of the heparinoid.

<Evaluation of Percutaneous Absorption Properties>
A percutaneous absorption test was performed on each of the obtained compositions for external use, using the same method as that of Experimental Example 1. An aqueous solution of uranine (1 mg/ml) was serially diluted (0.0001024 to 200 µg/ml) to prepare standard solutions for the calibration curves. Then, 200 µl of the sample obtained by the percutaneous absorption test or each of the standard solutions was added to each well of a 96-well plate. Then, the emission intensity at 535 nm was read by a plate reader (GENios manufactured by TECAN) at an excitation wavelength of 492 nm, and the amount of percutaneous permeation of uranine was determined from the reading. Furthermore, the amount of intradermal retention (µg) of uranine at 24 hours was similarly determined using an extract obtained by cryogenically grinding the skin after the test, and extracting it with 1 ml of purified water.

TABLE 7

| | | Comparative Example 5 | Example 42 |
|---|---|---|---|
| Oily-Phase Base | Light Liquid Paraffin | — | 95.9 |
| Surfactant | Glyceryl Monooleate | — | 3 |
| Aqueous-Phase Base | Water | 99.9 | 1 |
| Water-Soluble Substance | Fluorescein (Uranine) | 0.1 | 0.1 |
| Total (Weight %) | | 100 | 100 |
| Percutaneous Absorption Properties | Amount of Permeation (µg) at 2 Hours | 0 | 0 |
| | Amount of Permeation (µg) at 6 Hours | 0 | 36.56 |
| | Amount of Permeation (µg) at 24 Hours | 51.57 | 215.47 |
| | Amount of Intradermal Retention (µg) at 24 Hours | 1.74 | 3.48 |

The results are shown in Table 7. As is evident from Table 7, the composition for external use of the present invention was confirmed to have excellent percutaneous absorption properties even when it contains uranine as the water-soluble substance.

Experimental Example 3

<Preparation of Compositions for External Use>
Water-in-oil-type compositions for external use were obtained as in Experimental Example 1, except that the components were weighed to give the formulations shown in Table 8, and fluoresceinamine-labeled sodium hyaluronate (manufactured by PG Research, product code: FAHA-U2, molecular weight: 5,400 daltons) was used instead of the heparinoid.

<Evaluation of Percutaneous Absorption Properties>
A percutaneous absorption test was performed on each of the obtained compositions for external use, using the same method as that of Experimental Example 1. The standard substance of fluoresceinamine-labeled sodium hyaluronate was serially diluted (0.025 to 100 µg/ml) to prepare standard solutions for the calibration curves. Then, 100 µl of the sample obtained by the percutaneous absorption test or each of the standard solutions was added to each well of a 96-well plate. Then, the emission intensity at 518 nm was read by the Ensight multimode plate reader (manufactured by PerkinElmer Japan) at an excitation wavelength of 492 nm, and the amount of percutaneous permeation of fluoresceinamine-labeled sodium hyaluronate was determined from the reading.

TABLE 8

| | | Example 43 | Comparative Example 6 | Comparative Example 7 | Comparative Example 8 |
|---|---|---|---|---|---|
| Oily-Phase Base | Isopropyl Myristate | 94.49 | 98.99 | — | — |
| Surfactant | Glyceryl Monooleate | 4.5 | — | — | — |
| Aqueous-Phase Base | Water | 1 | 1 | 99.99 | — |
| | PBS | — | — | — | 100 |
| Water-Soluble Substance | Fluorescein-amine-Labeled Sodium Hyaluronate | 0.01 | 0.01 | 0.01 | — |
| Total (Weight %) | | 100 | 100 | 100 | 100 |
| Percutaneous Absorption Properties | Amount of Permeation (µg) at 24 Hours | 5.23 | 1.68 | 0.38 | 0.02 |

The results are shown in Table 8. As is evident from Table 8, the composition for external use of the present invention was confirmed to have excellent percutaneous absorption properties even when it contains sodium hyaluronate as the water-soluble substance.

Experimental Example 4

<Preparation of Compositions for External Use>
Water-in-oil-type compositions for external use were obtained as in Experimental Example 1, except that the components were weighed to give the formulations shown in Table 9, and FITC-labeled ovalbumin was used instead of the heparinoid.

FITC-labeled ovalbumin was prepared in accordance with the following procedure: 30 mg of ovalbumin was dissolved in 2 ml of a carbonate buffer at pH 9.3 to prepare an ovalbumin solution. Separately, 2.6 mg of FITC was dissolved in 20 µl of dimethylsulfoxide to prepare a FITC solution. The ovalbumin solution and the FITC solution were mixed, and then the mixture was allowed to stand at room temperature for 12 hours and reacted. Next, the reaction mixture was applied to gel chromatography (PD10 column manufactured by GE Healthcare Japan), and the eluted orange liquid was collected. This liquid was freeze-dried to obtain FITC-labeled ovalbumin.

<Evaluation of Percutaneous Absorption Properties>
A percutaneous absorption test was performed using a Franz cell, in accordance with the following procedure: A vertical Franz cell (model: TP-8S, manufactured by VIDREX) was fixed on a stirrer, and connected to a water bath and kept at about 32° C. Skin (about 1.5-cm square) excised from a pig (Yucatan micro pig) was placed in the Franz cell with the horny layer facing upward. The cap of the Franz cell was placed thereon and fixed with a clamp. Next, the receptor was filled with phosphate buffer (PBS), while avoiding the entry of air. Then, 200 μl of each of the compositions for external use obtained above was applied to the donor (1.77 cm²).

After 24 hours from the application, the skin was removed from the Franz cell, and the skin surface was washed with a 20% aqueous solution of ethanol. Then, the skin was cut into small pieces, and extraction was performed by immersing the skin in 500 μl of an extraction solvent (PBS: acetonitrile:methanol=2:1:1) for 24 hours. The extract was then filtered through a 0.20-μm filter (Advantec, 13HP020AN) to obtain a skin extract.

Using the extraction solvent, the standard substance of FITC-labeled ovalbumin was serially diluted (0.016 to 10 μg/ml) to prepare standard solutions for the calibration curves. Using a fluorometer (PerkinElmer, LS-55), fluorescence intensities (wavelength: 522.5 nm) of FITC were measured for the skin extract and the standard solutions prepared above, and the amount of FITC-labeled ovalbumin permeated into the skin (amount of intradermal retention at 24 hours) was quantified.

TABLE 9

|  |  | Example 44 | Comparative Example 9 |
|---|---|---|---|
| Oily-Phase Base | Isopropyl Myristate | 95.4 | — |
| Surfactant | Glyceryl Monooleate | 4 | — |
| Aqueous-Phase Base | Water | 0.5 | — |
|  | PBS | — | 99.9 |
| Water-Soluble Substance | FITC-Labeled Ovalbumin | 0.1 | 0.1 |
| Total (Weight %) |  | 100 | 100 |
| Percutaneous Absorption Properties | Amount of Permeation (μg) at 24 Hours | 5.91 | 0.04 |

The results are shown in Table 9. As is evident from Table 9, the composition for external use of the present invention was confirmed to have excellent percutaneous absorption properties even when it contains ovalbumin as the water-soluble substance.

The invention claimed is:

1. A composition for external use comprising a water-soluble fraction dispersed in an oily phase, wherein:
   the water-soluble fraction contains a surfactant and a solution in which a water soluble substance is dissolved in water,
   the water soluble substance is at least one selected from the group consisting of a protein and a polysaccharide, and
   the content of the water in the water-soluble fraction is 0.1 to 2.5% by weight of the total composition for external use.

2. The composition for external use according to claim 1, wherein the surfactant is a nonionic surfactant.

3. The composition for external use according to claim 1, wherein the surfactant is at least one selected from the group consisting of polyglycerin fatty acid esters, glycerin fatty acid esters, sorbitan fatty acid esters, polyoxyethylene hydrogenated castor oil, and sucrose fatty acid esters.

4. The composition for external use according to claim 1, wherein the content of the surfactant is 0.1 to 20% by weight of the total composition for external use.

5. The composition for external use according to claim 1, wherein the content of the water-soluble substance is 0.0001 to 2.5% by weight of the total composition for external use.

6. The composition for external use according to claim 5, wherein the oily phase contains a liquid oil.

* * * * *